United States Patent [19]

Wolf et al.

[11] Patent Number: 4,929,721
[45] Date of Patent: May 29, 1990

[54] POLYMERIZABLE AROMATIC-AZO-ALIPHATIC COMPOUNDS CAPABLE OF GENERATING PHOTOINITIATED FREE RADICALS

[75] Inventors: Richard A. Wolf, Midland, Mich.; Paul V. Grosso, West Hartford, Conn.

[73] Assignee: The Dow Chemical Company, Midland, Mich.

[21] Appl. No.: 213,208

[22] Filed: Jun. 29, 1988

[51] Int. Cl.$^5$ ................ C07C 107/02; C07C 107/04; C08G 63/100
[52] U.S. Cl. ................................... 534/885; 524/190
[58] Field of Search ........................... 534/885

[56] References Cited

U.S. PATENT DOCUMENTS

| | | | |
|---|---|---|---|
| 3,649,614 | 3/1972 | Sheppard et al. | 534/838 X |
| 3,763,129 | 10/1973 | Sheppard et al. | 534/838 X |
| 3,868,359 | 2/1975 | Sheppard et al. | 534/838 X |
| 3,882,007 | 5/1975 | Watanabe et al. | 534/838 X |
| 3,937,761 | 2/1976 | MacLeay et al. | 534/838 X |
| 3,957,750 | 5/1976 | MacLeay et al. | 534/838 X |
| 3,987,024 | 10/1976 | MacLeay et al. | 534/838 X |
| 4,029,615 | 6/1977 | Kamens et al. | 534/838 X |
| 4,086,224 | 4/1978 | MacLeay | 531/838 X |
| 4,094,868 | 6/1978 | Chandalia et al. | 534/838 X |
| 4,101,464 | 7/1978 | Kamens et al. | 534/838 X |

OTHER PUBLICATIONS

Porter et al., *Photorearrangement of an Unsymmetric Azo-Compound*, J. Chem. Soc., 1575, (1971).
Engel et al., *Thermolysis of Acyclic Azoalkanes: Simultaneous or Stepwise C-N Homolysis*, 105, J. Am. Chem. Soc., 6859, 6850, (1983).
Porter et al., *Cis-Intermediates in Azo-Compound Photolysis*, J. Chem. Soc., 263, 264, (1973).
Grundemann, *A New Method for the Preparation of α, β-Unsaturated Azo Compounds*, 8 Angew. Chem. Intern'l Ed. Eng., 459, (1969).
Brodka et al., *Darstellung Neuer Azo-Alkene und Derivate, Insbesondere Additionsprodukte CH-Acider Verbindungen*, 745 Liebigs Ann. Chem. 193, 195, (1971).
Schantl, *2-Phenylazo-2-Alkoxy-Propane*, 43 Tetrahedron Ltrs., 3785, (1970).
Kerber et al., *Synthese und Charakterisierung von Copolymeren aus Azo-Initiatoren und Styrol*, 177 Makromol. Chem., 1357-1371, (1976).
Kerber et al., *Pfropfung und Vernetzung Mittels Azogruppen Enthaltender Copolymerer*, 6, Makromol. Chem. 178, 1833-1839, (1977).
Kerber et al., *Über Die Copolymerisation von (3-Vinylphenylazo)-Methylmalonodinitril mit Styrol*, Makromol. Chem. 179, 1803-1814, (1978).
Nuyken et al., *Radical Efficiency and Ionic Reactions of some Unsymmetrical Azo Compounds*, Makromol. Chem. 184, 2251-2259, (1983).
Kerber et al., *Syntheses und Pfropfung azogruppenhaltiger Polycarbonate*, Makromol. Chem. 180, 609-614, (1979).
Oppenheimer et al., *The Synthesis of Blockcopolymers by Radical Polymerization*, Die Angewandte Makromol. Chem. 98, 167-184, (1981).
Smith, *The Thermal Decomposition of Azonitrile Polymers*, Die Makromol. Chem. 103, 301-303, (1967).
Furukawa et al., *Preparation of Block Copolymers with Macro-Azonitrile as an Initiator*, Angewandte Makromol. Chem. 1, 92-104, (1967).

Primary Examiner—Floyd D. Nigel

[57] ABSTRACT

Compounds of the formula:

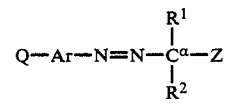

wherein
Q is a polymerizable olefin substituent;
Ar is an aromatic moiety;
$C^\alpha$ is the α carbon;
$R^1$ and $R^2$ are independently hydrogen or aliphatic groups; and
Z is a halogen, oxygen-containing, nitrogen-containing or sulfur-containing substituent complying with one of the formulae: —X, —OR, —SR or —$NR_2$, wherein X is a halogen and each R is independently a hydrogen atom or an aliphatic moiety;

contain azo groups which are stable with respect to thermal decomposition at high temperature (180° to 240° C. and beyond) in the absence of moderate light, so that such compounds may be polymerized and processed at ordinary polystyrene process temperatures. However, the azo group in those compounds or in polymers made from them decomposes to initiate free radical polymerization at temperature of 100° C. to 120° C. or less in the presence of moderate light.

14 Claims, No Drawings

POLYMERIZABLE AROMATIC-AZO-ALIPHATIC COMPOUNDS CAPABLE OF GENERATING PHOTOINITIATED FREE RADICALS

BACKGROUND OF THE INVENTION

The present invention pertains to the field of polymers containing active azo moieties and monomers for making those polymers.

Graft and block copolymers are copolymers wherein specific areas of the polymer contain different combinations of mer units. For instance, in a graft polymer a polymer backbone comprising one combination of mer units is attached to polymer branches which consist of a different combination of mer units. Such graft copolymers are conveniently made by forming a polymer backbone with initiator sites that may be used to initiate polymerization in a different monomer composition. Organic azo compounds are known to initiate free radicals at the site of the azo group through thermally, photolytically and chemically induced decomposition of the azo group.

Kerber et al. demonstrated that $\alpha,\alpha$-dicyanoethylazostyrene could be copolymerized with styrene at temperatures of about 0° C. to 60° C. to form a polystyrene backbone with pendant dicyanoethylazo moieties. The azo group could subsequently be decomposed by temperatures of about 70° C. or more to initiate polymerization in vinylic monomers. Kerber et al., *Synthese und Charakterisierung von Copolymeren aus Azo-Initiatoren und Styrol*, 177 Macromolecular Chem. 1357–1371 (1976): Kerber et al., *Propfung und Vernetzung mittels Azogruppen enthaltender Copolymerer6*, 178 Macromolecular Chem. 1833 (1977): Kerber et al., *Uber die Copolymerisation von (3-Vinylphenylazo)-methylmalonodinitril mit Styrol*, 179 Macromolecular Chem. 1803 (1978); Kerber et al., *Azoinitiatorn, 9)Synthese und Pfropfung azogruppenhaltiger Polycarbonate*, 180 Macromolecular Chem. 609 (1979).

The cyanoethyl-azo-styrene monomers and polymers of Kerber et al. share several problems which decrease their commercial utility. The azo group in the Kerber monomers and polymers is highly temperature sensitive and decomposes swiftly even at low temperatures of about 70° C. The polymer is unstable for extended shelf-life. Furthermore, the polymer cannot be formed or purified by processes which proceed at temperatures in excess of 70° C.

What is needed is a polymer containing pendant azo moieties which can be produced and processed at relatively high temperatures, which can be stored indefinitely at room temperature, and which can be easily activated to initiate polymerization at temperatures below that which causes thermal degradation of the polymer.

SUMMARY OF THE INVENTION

One aspect of the present invention is an azo compound comprising:
 (1) an azo group consisting of a first nitrogen atom and a second nitrogen atom;
 (2) an aromatic moiety bonded to the first nitrogen atom of said azo group, said aromatic moiety having a polymerizable olefin substituent; and
 (3) an aliphatic moiety bonded to the second nitrogen atom of said azo group, said aliphatic moiety having an oxygen-containing, nitrogen-containing, sulfur-containing or halogen substituent bonded to the $\alpha$ carbon thereof.

The $\alpha$ carbon of the aliphatic moiety is the carbon atom bonded to the second nitrogen atom of the azo group.

Another aspect of the present invention is a polymer comprising:
 (1) a polymer backbone having a plurality of pendant aromatic moieties:
 (2) a plurality of azo groups, each consisting of a first nitrogen atom and a second nitrogen atom and each bonded by said first nitrogen atom to one of the pendant aromatic moieties: and
 (3) an aliphatic group bonded to the second nitrogen atom of each azo group, said aliphatic group having an oxygen-containing, nitrogen-containing, sulfur-containing or halogen substituent bonded to its $\alpha$ carbon.

The azo groups in compounds and polymers of the present invention have a half-life of at least about 12 hours with regard to thermal decomposition at temperatures of about 130° C. in the absence of moderate light (for the purposes of this application, light refers to visible and ultraviolet light and preferably to light in about the visible spectrum). Therefore, the compounds may be polymerized or processed at relatively high temperatures and polymers may be stored at room temperature in the absence of light without substantial decomposition of the azo group.

On the other hand, the azo groups have a half-life of about 1 hour or less with respect to thermal decomposition at temperatures of about 120° C. in the presence of moderate light. If a compound of the present invention is copolymerized with styrene, acrylonitrile, butadiene or another polymer to form a polymer of the present invention, then the azo groups can be decomposed while the polymer is molten to liberate nitrogen which foams the polymer. The azo groups also yield free radicals sited on the pendant aromatic moieties which can initiate cross-linking within the polymer or polymerization with another monomer to form a graft copolymer, such as a polystyrene/polymethylmethacrylate graft copolymer.

DETAILED DESCRIPTION OF THE INVENTION

Compounds of the Present Invention

Compounds of the present invention comprise an azo group which consists of a first and a second nitrogen atom. The compounds may bear a plurality of azo groups per molecule, but each molecule preferably has only one azo group.

Compounds of the present invention comprise an aromatic moiety that is bonded to the first nitrogen atom of said azo group and has at least one substituent which has a polymerizable olefin moiety. The aromatic moiety may be heterocyclic but is preferably carbocyclic and more preferably hydrocarbyl. Although the size of the aromatic moiety is not critical to the invention, the aromatic moiety preferably comprises no more than about 10 carbon atoms: more preferably, no more than about 6 carbon atoms. The aromatic moiety may be, for example, arylene such as a phenylene or naphthylene group, or heterocyclic such as a pyridinylene, furanylene or thiophenylene group. Preferred examples are phenylene or naphthylene groups and the most preferred example is a phenylene group.

The aromatic group has a polymerizable olefin substituent. Its size is not critical as long as the size does not interfere with polymerization. The olefin substituent preferably comprises no more than about 6 carbon atoms: more preferably, no more than about 3 carbon atoms. It is most preferably a vinyl moiety. The olefin substituent is preferably meta to the azo group. Preferred examples of the olefin substituent are vinyl, vinylidene, isopropenyl, n-propenyl and n-butenyl groups.

Practical considerations such a steric hindrance limit the presence of other substituents on the aromatic moiety. Other substituents are preferably hydrocarbyl and more preferably alkyl. Other substituents preferably comprise no more than about four carbon atoms and more preferably no more than about two carbon atoms. Most preferably, the aromatic moiety has no other substituents. In their most preferred embodiments, the aromatic moiety and olefin substituent are combined to form a meta-styryl group.

Compounds of the present invention also comprise an aliphatic moiety bonded to the second nitrogen of the azo group. The $\alpha$ and $\beta$ carbons of the aliphatic moiety are preferably saturated. The aliphatic moiety is more preferably alkyl. Its size is not critical as long as it does not interfere with polymerization of the olefin substituent. It preferably comprises no more than about 12 carbon atoms: more preferably, no more than about 8 carbon atoms; and most preferably, no more than about 6 carbon atoms. The aliphatic moiety preferably comprises at least 2 carbon atoms and more preferably at least 3 carbon atoms. The carbon atom bonded to the azo group (the $\alpha$ carbon) is preferably bonded to one or two other carbon atoms: more preferably, to two other carbon atoms.

The aliphatic moiety has an oxygen-containing, nitrogen-containing, sulfur-containing or halogen substituent bonded to the $\alpha$ carbon. A halogen substituent consists of a halogen atom. An oxygen-containing, nitrogen-containing or sulfur-containing substituent comprises an oxygen, nitrogen or sulfur atom bonded by a single bond directly to the $\alpha$ carbon and bonded by single bonds to hydrogen atoms or aliphatic groups. For instance, the halogen, oxygen-containing, nitrogen-containing or sulfur-containing substituent comply with one of the formulae: $-X$, $-OR$, $-SR$ or $-NR_2$, wherein X is a halogen and each R is independently a hydrogen atom or an aliphatic moiety.

Aliphatic groups on the substituent (R) are preferably hydrocarbyl, more preferably alkyl. The size of aliphatic groups on the substituent (R) is not critical provided that they do not cause undue steric hindrance. They preferably comprise no more than about 6 carbon atoms: more preferably, no more than about 4 carbon atoms; and most preferably, no more than about 2 carbon atoms. The aliphatic groups may contain aromatic substituents but preferably do not. Examples of substituents on the $\alpha$ carbon include hydroxy, alkoxy, amino, alkylamino, alkylthio, thiol and halo groups. Preferably, the substituent is a halo, hydroxy or alkoxy group. More preferably it is hydroxy or alkoxy.

The aliphatic moiety bonded to the second nitrogen of the azo group and the oxygen-containing, nitrogen-containing, sulfur-containing or halogen substituent may combine to form, for example, a hydroxy-isopropyl group, a 1-hydroxycyclohexyl group, a hydroxymethyl group, a chloroisopropyl group, an aminoisopropyl group, a thiolisopropyl group, a methoxyisopropyl group or a methoxyisobutyl group. Most preferred embodiments are the hydroxyisopropyl, methoxyisopropyl and chloroisopropyl groups.

Azo compounds of the present invention are preferably represented by the formula:

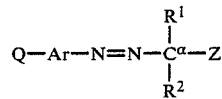

wherein
Q is a polymerizable olefin substituent:
Ar is an aromatic moiety:
$C^\alpha$ is the $\alpha$ carbon;
$R^1$ and $R^2$ are independently hydrogen or aliphatic groups; and
Z is a halogen, oxygen-containing, nitrogen-containing or sulfur-containing substituent complying with one of the formulae: $-X$, $-OR$, $-SR$ or $-NR_2$, wherein X is a halogen and each R is independently a hydrogen atom or an aliphatic moiety.

Q and Ar have the limitations and preferred embodiments previously set out to describe the aromatic moiety and its olefin substituent. Z has the limitations and preferred embodiments previously used to describe the oxygen-containing, nitrogen-containing, sulfur-containing or halogen substituent on the $\alpha$ carbon. $R^1$ and $R^2$ are each independently hydrogen atoms or aliphatic groups chosen such that the group of $R^1$, $R^2$, and $C^\alpha$ has the limitations and preferred embodiments used to describe the aliphatic moiety bonded to the second nitrogen atom of the azo group. For instance, $R^1$ and $R^2$ together preferably comprise no more than about 11 carbon atoms, more preferably no more than about 7 carbon atoms and more highly preferably no more than about 5 carbon atoms. They are preferably hydrocarbyl and more preferably alkyl. Most preferably, $R^1$ and $R^2$ are each methyl.

Highly preferred azo compounds of the present invention are represented by the formula:

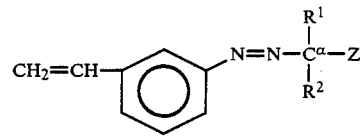

wherein each character has the meaning previously defined.

Compounds of the present invention are prepared from olefin-bearing aromatic hydrazines, which are made from the corresponding olefin-bearing aromatic amine or nitrate by the procedure described in Arcus and Schaffer, *m-Hydrazinostyrene*, 1958 J. Chem. Soc. 2428 (1958), which is incorporated herein by reference. The aromatic moiety and olefin substituent of the amine or nitrate form the aromatic group (Ar) and the olefin substituent (Q) of the finished compound.

First, the olefin-bearing aromatic amine, such as aminostyrene, is prepared by reaction of the corresponding nitrate with stannous chloride in the presence of acid, such as concentrated hydrochloric acid, and alcohol such as ethanol, at ambient temperatures or with heating. Conditions are described in Bigge, et al., *Palladium-Catalyzed Coupling Reactions of Uracil Nucleosides and Nucleotides*, 102 J. Am. Chem. Soc. 2033, 2036 (1980), which is incorporated herein by reference.

Second, the amine is converted to a vinyl-aromatic diazonium ion such as m-styryldiazonium ion by reaction with cold aqueous sodium nitrite, for instance at about 0° C. If long storage is desired, the solution may be washed with aqueous fluoboric acid: the diazonium fluoborate can be stored for years at −10° C. under dry conditions.

Third, the diazonium ion or fluoborate salt is converted to the corresponding hydrazine hydrochloride by reaction with stannous chloride in the presence of hydrochloric acid. The hydrazine hydrochloride may be stored for months under dry conditions at about 10° C. At the time for use, the basic hydrazine may be generated by extraction from 2N sodium hydroxide with methylene chloride, or similar techniques.

The hydrazine is contacted with a ketone or aldehyde, such as acetone or propanal, at cool temperatures, such as about 10° C., in a solvent, such as methanol, to form an aliphatic-aryl hydrazone. The aliphatic group of the ketone forms the aliphatic group of the hydrazone, and subsequently is the aliphatic group attached to the second azo nitrogen of the final product (represented by $R^1$, $R^2$ and $C^\alpha$). The addition of acyl compounds to aromatic hydrazines to form aromatic hydrazones is well-known in the art and is described in Ardagh et al., "An Investigation of Some Properties of Phenylhydrazine and Factors Affecting Hydrazone Formation," 47 *J. Am. Chem. Soc.* 2976 (1925), which is incorporated herein by reference.

The hydrazone reacts at ambient temperatures with a haloacid, alcohol, amine or thiol (Z-H) in the presence of anhydrous sodium acetate and iodine crystals to form the aliphatic-aryl azo compound product with a halogen, oxygen-containing, nitrogen-containing or sulfur-containing substituent (Z) attached to the $\alpha$ carbon of the aliphatic group.

The solution containing the azo compound is added to aqueous sodium nitrite, for instance a 12.6 percent solution. Thereafter, the remaining reagents are neutralized with sodium sulfite, sodium hydroxide and water, and the product is purified by known processes such as rotoevaporation, extraction, filtration and fractional distillation. Conditions for addition to the hydrazone and its conversion to an azo compound are known in the art and reported in J. Schantl, "2-Phenylazo-2-alkoxypropane", 43 *Tetrahedron Letters* 3785 (1970), which is incorporated herein by reference.

The azo group in a compound of the present invention is substantially stable with respect to thermal decomposition in the absence of light. The group is considered substantially stable if its half-life is at least about 12 hours and preferably at least about 24 hours. Compounds of the present invention are substantially stable at about 130° C.; preferably, at about 180° C.; and more preferably, at about 240° C. The half-life of those compounds is most preferably at least about 1 hour at about 290° C. The half-life at in the absence of moderate light is most preferably months at room temperature and days at between about 130° C. and about 240° C.

Polymers of the Present Invention

Because of their stability in the absence of light, compounds of the present invention can readily be incorporated into polymers in the absence of moderate light by polymerization of the olefin moiety without causing substantial decomposition of the azo group. The polymers into which compounds of the present invention are incorporated are those which may contain styryl mer units. For instance, compounds of the present invention may be copolymerized with monomers such as styrene, acrylonitrile, butadiene, methyl methacrylate or other unsaturated monomers. Compounds of the present invention are preferably incorporated into polystyrene, styrene-acrylonitrile (SAN), styrene-butadiene (SB) and acrylonitrile-butadiene-styrene (ABS) type polymers. More preferably, compounds of the present invention are copolymerized with styrene or made part of SAN type polymers.

The ratio of azo bearing monomers to other monomers used in making the polymer will depend to a great extent upon the desired use for the azo group. For instance, if the azo group is intended to initiate cross-linking or further polymerization, the proportion of azo bearing monomers will reflect the desired density of cross-linking or grafting of polymer. Compounds of the present invention preferably make up no more than about 10 percent of the monomers used to make the polymer; more preferably, no more than about 5 percent; and most preferably, no more than about 2 percent. Compounds of the present invention preferably make up at least about 0.01 percent of the monomers used to make the polymer; more preferably, at least about 0.1 percent and most preferably, at least about 1 percent.

Compounds of the present invention may be polymerized by any method known for polymerizing styrene monomer, as long as the method does not require substantial exposure to temperatures at which the azo group is not substantially stable. For instance, the polymer may be formed in temperatures of up to about 240° C., more preferably up to about 180° C., as long as the polymer is not subjected to moderate light.

Conditions and methods for such polymerization are well-known to persons skilled in the art. For instance, the polymerization may be carried out by a free radical mechanism using initiators such as azo diisobutyronitrile (AIBN), peroxides, oxidation-reduction systems and the like. Polymerization is carried out by mixing the monomers and initiator in a reaction vessel and then subjecting the initiator to temperatures at which the initiator decomposes generating free radicals to initiate polymerization. Among known initiators, for instance, benzoyl peroxide will initiate polymerization at temperatures from about 55° C. to about 115° C., and AIBN will initiate polymerization at temperatures from about 70° C. to about 100° C. Polymerizations are described in Overberger, "Bulk Polymerization with Peroxide Catalyst," 1 *Macromolecular Synthesis* 5 (1977 J. Moore ed.) and Ingram et al., "Expandable Polystyrene Beads," 1 *Macromolecular Synthesis* 349 (1977 J. Moore ed.), which are incorporated herein by reference.

Anionic mechanism polymerization can also be initiated by an organometallic compound such as n-butyllithium. The initiator is added under vacuum at a low temperature, such as about 0° C. to 30° C., to a purified mixture of monomer, a solvent such as benzene and an accelerant such as tetrahydrofuran. Such a reaction is fully described in Fetters et al., "Polystyrene with Predictable Molecular Weights and Uniform Molecular Weight Distributions," 1 *Macromolecular Synthesis* 463 (1977 J. Moore ed.), which is incorporated herein by reference.

Cationic method polymerization can be initiated by a known cationic initiator, such as stannic chloride. Stannic chloride is dried and dissolved in a solvent such as carbon tetrachloride in a concentration of about 2 percent by weight. The initiator is added to dried monomer in a solvent, such as carbon tetrachloride and nitrobenzene, under low temperatures such as about 0° C. Such a polymerization is described fully in Overberger, "Solution Polymerization with Cationic Catalysis", 1 *Macromolecular Synthesis* 6 (1977 J. Moore ed.), which is incorporated herein by reference.

Compounds of the present invention may also be polymerized by known methods of emulsion polymerization, suspension polymerization, solution polymerization or thermally initiated polymerization.

The polymers of the present invention generally comprise a polymer backbone having a plurality of pendant aromatic moieties. At least some of the pendant aromatic moieties are bonded to the first nitrogen atom of an azo group. The second nitrogen atom of each azo group is bonded to an aliphatic moiety having an oxygen-containing, nitrogen-containing, sulfur-containing or halogen substituent on the α carbon. The aromatic moieties, aliphatic moieties and substituents on the α carbon all have the same preferred limitations set out previously in describing the compounds of the present invention.

Polymers of the present invention preferably are represented by the formula:

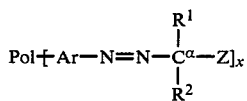

wherein Pol represents the polymer backbone, x represents a number of azo-bearing pendant moieties of 1 or more, and all other characters have the meanings given previously in describing the compounds. Polymers of the present invention are more preferably represented by the formula:

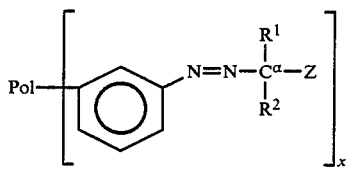

wherein all characters have the meanings given previously.

Preferably, no more than about 10 percent of the mer units in the polymer have pendant azo moieties; more preferably, no more than about 5 percent: and most preferably, no more than about 2 percent. Preferably, at least 0.01 percent of the mer units in the polymer have pendant azo moieties: more preferably, at least about 0.1 percent: and most preferably, at least about 1 percent. Polymers of the present invention may be mixed with other known agents, such as fillers, dyes, compatibilizing and stabilizing agents, etc.

The stability of the azo groups in polymers of the present invention is similar to the stability of azo groups in compounds of the present invention in the absence of light, and follows the same limits and preferred embodiments. The half-life in the absence of moderate light is preferably at least months at room temperature and days at between about 130° C. and about 240° C.

On the other hand, the azo groups in polymers and compounds of the present invention undergo substantial thermal decomposition in the presence of moderate light at moderate elevated temperatures. Light means any light in about the ultraviolet or visible spectrum; preferably light in about the visible spectrum; and more preferably, light with a wavelength of about 350 to about 450 nanometers. Moderate light is light with an intensity sufficient to accelerate thermal decomposition of the azo group. It preferably has an intensity of no less than about 0.01 W/cm$^2$, and more preferably has an intensity of no more than about 0.2 W/cm$^2$.

The group undergoes substantial thermal decomposition if its half-life is at most about 1 hour; preferably, at most about 30 minutes: and more preferably, at most about 15 minutes. In the presence of moderate light, azo groups in polymers and compounds of the present invention preferably undergo substantial thermal decomposition at about 120° C.; more preferably at about 100° C.; and most preferably at about 70° C. In the presence of moderate light the azo moiety most preferably has a half-life of no more than about 10 minutes at 100° C.

The decomposition of azo groups in polymers of the present invention may be used advantageously to form graft polymers. A polymer of the present invention can be subjected to heat and light in the presence of unsaturated monomers, such as vinyl chloride, methyl methacrylate, styrene, propylene, ethylene or other known monomers, to initiate polymerization of new strands of polymer attached to the polymer of the present invention. Conditions for such a polymerization are similar to those for known free radical polymerizations, except that the light and temperature conditions must be those appropriate to decompose azo groups in the polymer of the present invention. The azo group in a polymer of the present invention can also be decomposed in the absence of other monomers to cause cross-linking within the polymer itself.

ILLUSTRATIVE EXAMPLES

The following examples are for illustrative purposes only and do not limit the scopes of either the claims or the specification. For the purposes of these examples all parts and percentages are by weight unless otherwise specified.

EXAMPLE 1

Preparation of 2-Methoxyisopropylazo-m-styrene

A 500-ml round-bottom flask is charged with 15.41 g of m-nitrostyrene in 80 ml of methanol. The flask is stirred and cooled in an ice bath. A solution of 70.18 g of SnCl$_2$2H$_2$O in 130 ml of concentrated (37 percent) aqueous hydrochloric acid is added slowly. After addition, the flask is removed from the ice water bath and heated with a warm water bath to 35° C. over a period of one hour. The flask is stored in a refrigerator for several hours.

Water (20 ml) is added to the flask and the precipitate is broken up. The flask is placed in an ice water bath and a solution of 7.34 g of sodium nitrate in 25 ml of water is added slowly. A solution of 47 g of stannous chloride dihydrate in 90 ml of 37 percent aqueous hydrochloric acid is added over a 20-minute period. The reaction mixture is stirred for another hour and then stoppered and stored for 2 days. The white solid precipitate is collected by filtration and air dried. Subsequently, the precipitate is dried in a vacuum desiccator. The precipitate comprises 12.5 g of m-styrylhydrazine hydrochloride.

A 7.38 mmole sample of m-styrylhydrazine hydrochloride is extracted from 2N sodium hydroxide into methylene chloride. A substantial excess of acetone is added and stirred for 30 minutes. The unreacted acetone and solvent are removed by rotary evaporation, and 30 ml of methanol is added with stirring at ambient temperature. Sodium acetate (1.33 g) and 2.10 g of iodine are added and the solution is permitted to stir at ambient temperature for several hours. A 12.6 percent solution of sodium nitrite (5 ml) is added to the reaction mixture. The reaction mixture is filtered and solids are washed with methanol and diethyl ether. After removing the solvents under vacuum, the residue is extracted several times with pentane and the pentane solution is dried with anhydrous sodium sulfate. Removal of pentane under vacuum leaves 0.87 g of the title compound, an orange-red oil.

EXAMPLE 2

Preparation of Copolymer with Styrene Monomer

A screwcap bottle is filled with 0.08 g of 2-methoxyisopropylazo-m-styrene and 7.928 g of styrene monomer (about 0.5 percent azo-bearing monomer by mole). The contents are sparged with argon for 35 minutes at ambient temperature and the bottle is tightly capped. The bottle is heated in a silicone oil bath at 132° C. for 21.5 hours and then allowed to cool to ambient temperature. The resulting polymer is washed with pentane and provides an 85 percent yield of polymer. The polymer is dissolved in 70 ml of toluene and poured into 400 ml of methanol. After stirring for several hours, the precipitate is filtered off and air dried. The product polymer is analyzed by UV-visible spectroscopy and shows a weak absorption with a maximum at 400 to 430 nanometers.

EXAMPLE 3

Alternate Copolymerization Method

A 100-ml round-bottom flask is charged with 0.52 g of 2-methoxyisopropylazo-m-styrene and 51.48 g of styrene monomer (about 0.5 percent azo-bearing monomer by mole) with 0.41 g of AIBN initiator. The flask is covered with a rubber septum and wired shut. The solution is sparged with argon at 70° C. for 4 minutes. The flask is heated to 71° C. for 19 hours. AIBN initiator (0.2 g) is added followed by further argon sparging. The reaction mixture is heated to 75° C. for 4 more hours. The solid product is purified and isolated as described in Example 2 to provide a 95.1 percent yield of copolymer. The UV-visible spectrum of the copolymer has an absorption peak at 405 nanometers.

EXAMPLE 4

Photoinduced Grafting of Methyl Methacrylate onto Copolymer

The copolymer (3 g) from Example 3 is added to a round-bottom flask with 7.5 g of methyl methacrylate. The flask is sparged with argon for 10 minutes to remove dissolved oxygen. The flask is heated to 67° C. in a hot water bath and positioned 8 cm from the bulb of a medium intensity visible lamp (BLAK-RAY ® Model B-100A, 100 watts) whose intensity is about 0.18 W/cm² at about 5 cm from the bulb. After 7.58 hours, the flask is removed from the light and heat and the contents are poured into 600 ml of methanol. The methanol solution is stirred at ambient temperatures for several hours and solids are removed by filtration. The product comprises 5.01 g of a graft copolymer of poly(methyl methacrylate) grafted to polystyrene.

EXAMPLE 5

Photoinduced Grafting of Methyl Methacrylate onto Copolymer

Example 4 is repeated using a similar polymer except that it comprises only 0.25 mole percent azo-bearing mer units in styryl mer units. The temperature of the hot water bath is 63° C. and the reaction is permitted to run for about 6 hours. The product comprises 4.33 g of a graft copolymer of poly(methyl methacrylate) grafted to polystyrene.

EXAMPLE 6

Cast Film of Polystyrene/Polymethyl Methacrylate Graft Copolymer

A 5 percent solution of the graft copolymer from Example 5 in toluene is prepared. A separate 5 percent solution of polystyrene and poly(methyl methacrylate) in toluene is prepared as a control. Each solution (1.5-g samples) are placed in separate 5-cm crystallizing dishes and allowed to air dry for 24 hours. The control mixture forms an opaque white film. The graft copolymer mixture forms a clear film with a slight haze on one side. The graft copolymer film is tougher and less brittle when broken with a spatula.

What is claimed is:

1. An azo compound comprising:
   (1) an azo group;
   (2) an aromatic moiety bonded to one nitrogen atom of said azo group, said aromatic moiety having a polymerization olefin substituent; and
   (3) an aliphatic moiety bonded to the other nitrogen atom of said azo group, said aliphatic group having an oxygen-containing, nitrogen-containing, sulfur-containing or halogen substituent bonded to the α carbon thereof
wherein the olefin moiety comprises no more than about 6 carbon atoms; the aromatic moiety is a carbocyclic group with no more than about 10 carbon atoms; the aliphatic moiety comprises no more than about 12 carbon atoms; and the substituent on the α carbon is a hydroxy, alkoxy, amine, aminoalkyl, thioalkyl, thiol or halo group.

2. The compound of claim 1 wherein the azo group has a half-life of at least 12 hours with regard to thermal decomposition at about 180° C. in the absence of moderate light.

3. The compound of claim 2 wherein the azo group has a half-life of no more than about one hour with respect to thermal decomposition at about 120° C. in the presence of moderate light.

4. The compound of claim 3 wherein the azo group has a half-life of at least about 12 hours with regard to thermal decomposition at about 240° C. in the absence of moderate light.

5. The compound of claim 4 wherein the azo group has a half-life of no more than about 15 minutes with regard to thermal decomposition at about 100° C. in the presence of moderate light.

6. The compound of claim 3 wherein the olefin moiety can be polymerized in the absence of moderate light without causing substantial decomposition of the azo group.

7. The compound of claim 1 wherein the substituent on the α carbon is hydroxy or alkoxy.

8. The compound of claim 1 which complies with the formula:

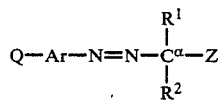

wherein
- Q is the olefin moiety;
- Ar is the aromatic moiety;
- $C^\alpha$, $R^1$ and $R^2$ are together the aliphatic moiety; and
- Z is a halogen, oxygen-containing, nitrogen-containing or sulfur-containing substituent complying with one of the formulae: —X, —OR, —SR or —NR$_2$, wherein X is a halogen and each R s independently a hydrogen atom or an aliphatic moiety comprising no more than 4 carbon atoms.

9. The compound of claim 1 wherein the olefin moiety comprises no more than about 3 carbon atoms; the aromatic moiety comprises a phenylene ring; the aliphatic moiety comprises no more than about 8 carbon atoms; and the substituent on the α carbon is a hydroxy, alkoxy, or halo group.

10. The compound of claim 9 wherein the olefin and aromatic moieties make up a meta-styryl moiety and the aliphatic moiety is an alkyl group with no more than about 6 carbon atoms.

11. The compound of claim 10 which complies with the formula:

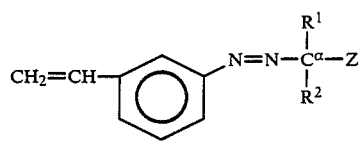

wherein Z is a hydroxy, alkoxy or halogen moiety: and $R^1$ and $R^2$ are alkyl groups or hydrogen atoms chosen such that $C^\alpha$, $R^1$ and $R^2$ together comprise from 2 to 6 carbon atoms.

12. The compound of claim 10 wherein the aliphatic group attached to the second nitrogen atom of the azo group and the oxygen-containing or halogen substituent considered together form a 1-hydroxycyclohexyl group, a hydroxymethyl group, a chloroisopropyl group, a methoxyisopropyl group or a methoxyisobutyl group.

13. The compound of claim 12 wherein the aliphatic group attached to the second nitrogen atom of the azo group and the oxygen-containing or halogen substituent considered together form a chloroisopropyl group, a methoxyisopropyl group or a methoxyisobutyl group.

14. The compound of claim 13 which is 2-methoxyisopropylazo-m-styrene or 2-hydroxyisopropylazo-m-styrene.

* * * * *